US006077511A

United States Patent [19]
Langedijk

[11] Patent Number: 6,077,511
[45] Date of Patent: Jun. 20, 2000

[54] ANTIGENIC PEPTIDE DERIVED FROM THE G PROTEIN OF RSV FOR TYPE- AND SUBTYPE-SPECIFIC DIAGNOSIS OF RESPIRATORY SYNCYTIAL VIRUS (RSV) INFECTION

[75] Inventor: Johannes Petrus Maria Langedijk, Amsterdam, Netherlands

[73] Assignee: Instituut voor Dierhouderij en Diergezondheid, Lelystad, Netherlands

[21] Appl. No.: 08/793,792

[22] PCT Filed: Aug. 22, 1995

[86] PCT No.: PCT/NL95/00279

§ 371 Date: Feb. 25, 1997

§ 102(e) Date: Feb. 25, 1997

[87] PCT Pub. No.: WO96/06112

PCT Pub. Date: Feb. 29, 1996

[30] Foreign Application Priority Data

Aug. 25, 1994 [EP] European Pat. Off. ............... 94202440

[51] Int. Cl.$^7$ .................. A61K 39/155; C07K 14/10; C07K 14/115; C12Q 1/70
[52] U.S. Cl. .................. 424/186.1; 530/324; 530/387.9; 530/388.3; 530/389.4; 424/192.1; 424/193.1; 424/211.1; 435/5
[58] Field of Search .................. 424/186.1, 211.1, 424/192.1, 193.1; 435/5; 514/12; 530/324, 387.9, 388.3, 389.4

[56] References Cited

FOREIGN PATENT DOCUMENTS

| 92/01471 | 2/1992 | WIPO | ............ A61K 39/00 |
| WO 92/01471 | 2/1992 | WIPO . | |
| 95/27787 | 10/1995 | WIPO | ............ C12N 15/45 |
| WO 95/27787 | 10/1995 | WIPO . | |

OTHER PUBLICATIONS

Norrby, E. et al. Proceedings of the National Academy of Sciences (USA), vol. 84, pp. 6572–6576, 1987.

Åkerlind–Stopner et al., "A Subgroup–Specific Antigenic Site in the G Protein of Respiratory Syncytial Virus Forms a Disulfide–Bonded Loop," *Journal of Virology*, vol. 64, No. 10, pp. 5143–5148, Oct. 1990.

Cane et al., "Identification of variable domains of the attachment (G) protein of subgroup A respiratory syncytial viruses," *Journal of General Virology*, vol. 72, pp. 2091–2096, 1991.

Edwards, Alvin J., "The Effect of Stressors Like Rumen Overload and Induced Abortion on BRD in Feedlot Cattle," *Agri–Practice*, vol. 10, No. 2, pp. 10–15, Mar./Apr. 1989.

Felsenstein, J., "PHYLIP—Phylogeny Inference Package (Version 3.2)", *Cladistics*, 5, pp. 164–166, 1989.

(List continued on next page.)

*Primary Examiner*—Mary E. Mosher
*Attorney, Agent, or Firm*—Trask, Britt & Rossa

[57] ABSTRACT

Antigenic substance or precursor thereof comprising a peptide part derived from an amino acid sequence located between two mucin-like regions of a protein G of a respiratory syncytial virus (RSV). Said antigenic substance or precursor thereof allows to discriminate between, or identify, different types or subtypes of respiratory syncytial viruses, or antibodies against them. In preferred embodiments, the peptide part is derived from protein G of bovine respiratory syncytial virus, human respiratory syncytial virus A, human respiratory syncytial virus B, or ovine respiratory syncytial virus. Use of the antigenic substance or precursor thereof (in vaccines) for prophylaxis of RSV infections, in assays and testkits for detecting or identifying (antibodies against) RSV types or subtypes, and in methods for obtaining antibodies against RSV types or subtypes. Use of such antibodies in assays and testkits for detecting or identifying RSV types or subtypes.

22 Claims, 8 Drawing Sheets

OTHER PUBLICATIONS

Fields et al., "HBTU Activation for Automated Fmoc Solid–Phase Peptide Synthesis," *Peptide Research*, vol. 4, No. 2, pp. 95–101, 1991.

Furze et al., "Antigenic heterogeneity of the attachment protein of bovine respiratory syncytial virus," *Journal of General Virology*, vol. 75, pp. 363–370, 1994.

Healy et al., "Morbidity and Mortality in a Large Irish Feedlot; Microbiological and Serological Findings in Cattle with Acute Respiratory Disease," *British Veterinary Journal*, vol. 149, No. 6, pp. 549–560, 1993.

Jentoft, Neil, "Why are proteins O–glycosylated?," *TIBS*, vol. 15, pp. 291–294, Aug. 1990.

Johnson et al., "The G glycoprotein of human respiratory syncytial viruses of subgroups A and B: Extensive sequence divergence between antigenically related proteins," *Proc. Natl. Acad. Sci. USA*, vol. 84, pp. 5625–5629, Aug. 1987.

Lerch et al., "Nucleotide Sequence Analysis and Expression from Recombinant Vectors Demonstrate That the Attachment Protein G of Bovine Respiratory Syncytial Virus is Distinct from that of Human Respiratory Syncytial Virus," *Journal of Virology*, vol. 64, No. 11, pp. 5559–5569, Nov. 1990.

Mallipeddi et al., "Analysis of the ovine respiratory syncytial virus (RSV) G glycoprotein gene defines a subgroup of ungulate RSV," *Journal of General Virology*, vol. 74, pp. 2787–2791, 1993.

Mallipeddi et al., "Sequence variability of the glycoprotein gene of bovine respiratory syncytial virus," *Journal of General Virology*, vol. 74, pp. 2001–2004, 1993.

Norrby et al., "Site–directed serology with synthetic peptides representing the large glycoprotein G of respiratory syncytial virus," *Proc. Natl. Acad. Sci. USA*, vol. 84, pp. 6572–6576, Sep. 1987.

Saitou et al, "The Neighbor–joining Method: A New Method for Reconstructing Phylogenetic Trees," *Mol.Biol. Evol.*, vol. 4, No. 4, pp. 406–425, 1987.

Satake et al., "Respiratory syncytial virus envelope glycoprotein (G) has a novel structure," *Nucleic Acids Research*, vol. 13, No. 21, pp. 7795–7812, 1985.

Sullender et al., "Genetic Diversity of the Attachment Protein of Subgroup B Respiratory Syncytial Viruses," *Journal of Virology*, vol. 65, No. 10, pp. 5425–5434, Oct. 1991.

Van der Poel et al., "Dynamics of bovine respiratory syncytial virus infections: a longitudinal epidemiological study in dairy herds," *Archives of Virology*, vol. 133, pp. 309–321, 1993.

Welliver, Robert C., "Detection, Pathogenesis, and Therapy of Respiratory Syncytial Virus Infections," *Clinical Microbiology Reviews*, vol. 1, No. 1, pp. 27–39, Jan. 1988.

Wensvoort et al., "Production of Monoclonal Antibodies Against Swine Fever Virus and Their Use in Laboratory Diagnosis", *Veterinary Microbiology*, vol. 12, pp. 101–108, 1986.

Wertz et al., "Nucleotide sequence of the G protein gene of human respiratory syncytial virus reveals an unusual type of viral membrane protein," *Proc. Natl. Acad. Sci. USA*, vol. 82, pp. 4075–4079, Jun. 1985.

Westenbrink et al., "Comparison of a newly developed enzyme–linked immunosorbent assay with complement fixation and neutralisation tests for serology of bovine respiratory syncytial virus infections", *Res. Vet. Sci.*, vol. 38, pp. 334–340, 1985.

Stott et al., "Respiratory Syncytial Virus: Brief Review", *Arch. Virol.*, 84, pp. 1–52, 1985.

BRSV

ORSV

HRSV-B

HRSV-A

FIG.5A

BRSV

ORSV

HRSV-B

HRSV-A

FIG.5B

ANTIGENIC PEPTIDE DERIVED FROM THE G PROTEIN OF RSV FOR TYPE- AND SUBTYPE-SPECIFIC DIAGNOSIS OF RESPIRATORY SYNCYTIAL VIRUS (RSV) INFECTION

This is a 371 of International Application PCT/NL95/00279, filed Aug. 22, 1995.

FIELD OF THE INVENTION

This invention relates to the fields of peptide-based diagnostics and vaccines in connection with diseases caused by or related with respiratory syncytial virus (RSV) infection.

The invention involves a so far unidentified small, independently folding, globular protein module between mucin-like regions in the attachment protein G of RSV, and its use. More specifically, the invention relates to the design of an antigenic substance, preferably peptide-based, corresponding to said protein module in the attachment protein G of RSV, that can be used as a basis for e.g. a diagnostic assay. Peptides corresponding to this independently folding globular protein can also be incorporated in vaccines along with other peptides to induce protective immune responses to the virus.

BACKGROUND OF THE INVENTION

RSV infections are a major cause of respiratory tract disease in humans, cattle, sheep and goats (Stott and Taylor, 1985). The virus is classified within the Pneumovirus genus of the Paramyxoviridae. Human respiratory syncytial virus (HRSV) is the most important causative agent of bronchiolitis and pneumonia in infants and young children. Approximately 100,000 children are hospitalized each year in the USA as a result of RSV infection. A vaccine against the virus is not available and development of a vaccine is third—subsequent to Malaria and Human Immunodeficiency Virus—on the priority list of the World Health Organization. In cattle, respiratory disease is one of the most frequently recorded diseases. Recent reports indicate that respiratory disease can account for up to 60% of morbidity and for around 60% of mortality in feedlot cattle (Healy et al., 1993, Edwards, 1989). Bovine respiratory syncytial virus (BRSV) infections are the major cause of respiratory disease in calves resulting in high economic losses.

Because different antigenic subgroups are described for HRSV and BRSV (Johnson et al., 1987, Furze et al., 1994), it is important to monitor the prevailing subgroups in a population to choose a candidate vaccine of the right subgroup(s)

The virus has two major surface glycoproteins: the attachment protein G and the fusion protein F. The G protein is unique for RSV, it is highly variable between HRSV subgroups (53% amino acid homology; Johnson et al., 1987), or between HRSV and ungulate RSV (30% amino acid homology; Lerch et al., 1990). However, within the subgroups the amino acid homology is much larger (80% or more within several HRSV-A strains; Cane et al., 1991), 90% or more within several HRSV-B strains (Sullender et al., 1991) and 90% or more within four BRSV strains (Mallipeddi and Samal, 1993a). The G protein shares neither sequence nor structural homology with other attachment proteins of other Paramyxoviruses (Satake et al., 1985, Wertz et al., 1985). In contrast to the attachment proteins of other paramyxoviruses, G is shorter and lacks hemagglutination or neuraminidase activity. RSV-G is a type II membrane protein and contains about 60% carbohydrate by weight. Approximately 20% of the carbohydrate moieties are N-linked carbohydrates and 80% are O-linked carbohydrates which are linked to the unusually high number of hydroxy amino acids in the protein.

A number of diagnostic assays (reviewed by Welliver, 1988) are available for the detection of RSV. However, these assays are based on whole virus or complete proteins that do not (effectively) discriminate between subgroups of HRSV nor between different RSV types. Because the F protein is highly conserved between all RSV types, a discriminating assay is hard to design based on protein F and should therefore include at least a part of the more variable G protein.

Empirical methods to determine the immunodominant site on BRSV-G and HRSV-G showed that the immunodominant site of the peptide was located within the C-terminal half of this peptide (residues 174–188; Norrby et al., 1987). It has been suggested that a 15-residue peptide (residues 174–188) could be used for subtype-specific site-directed serology (Akerlind-Stopner et al., 1990, Norrby et al., 1987).

The use of peptides as antigens in serological diagnosis of infections has gained interest, because peptides are cheap and easy to produce in a reproducible manner. However, the use of peptides in routine diagnosis has so far been limited due to lack of sensitivity.

SUMMARY OF THE INVENTION

The invention provides a peptide comprising an amino acid sequence derived from protein G of a respiratory syncytial virus, wherein said amino acid sequence has a length of from about 28 to about 37 amino acid residues and is derived from a region of said protein G which is located between two mucin-like regions. Preferably, said amino acid sequence comprises at least the amino acid residues Nos. 159–186, such as comprising the amino acid residues Nos. 159–186 or Nos. 157–193 of protein G (according to the numbering of protein G of bovine respiratory syncytial virus) and has at most 4 amino acid differences therewith. Preferably, said respiratory syncytial virus (RSV) is selected from the group consisting of bovine respiratory syncytial virus (BRSV), human respiratory syncytial virus A (HRSV-A), human respiratory syncytial virus B (HRSV-B), and ovine respiratory syncytial virus (ORSV).

Said amino acid sequence preferably comprises a member selected from the group consisting of

HQDHNNFQTLPYVPCSTCEGNLACLSLC (SEQ ID NO: 1),

QQDYSDFQILPYVPCNICEGDSACLSLC (SEQ ID NO: 2),

PKDDYHFEVFNFVPCSICGNNQLCKSIC (SEQ ID NO: 3),

PNNDFHFEVFNFVPCSICSNNPTCWAIC (SEQ ID NO: 4);

more preferably a member selected from the group consisting of

NHQDHNNFQTLPYVPCSTCEGNLACLSLCHIE (SEQ ID NO: 5),

IQQDYSDFQILPYVPCNICEGDSACLSLCQDR (SEQ ID NO: 6),

KPKDDYHFEVFNFVPCSICGNNQLCKSICKTI (SEQ ID NO: 7),

KPNNDFHFEVFNFVPCSICSNNPTCWAICKRI (SEQ ID NO: 8);

such as a member selected from the group consisting of

ENHQDHNNFQTLPYVPCSTCEGNLA-CLSLCHIETERA (SEQ ID NO: 9),
EIQQDYSDFQILPYVPCNICEGDSACLSLCQDRSESI (SEQ ID NO: 10),
KKPKDDYHFEVFNFVPCSICGNNQLCK-SICKTIPSNK (SEQ ID NO: 11),
NKPNNDFHFEVFNFVPCSICSNNPTCWA-ICKRIPNKK (SEQ ID NO: 12).

It is preferable that the peptide is capable of adopting the tertiary structure of its counterpart in the corresponding G protein.

This invention also relates to an antigenic substance, or a precursor thereof, which allows discrimination between or identification of different RSV types or subtypes, or allows discrimination between or identification of antibodies against different RSV types or subtypes, which antigenic substance or precursor thereof comprises a peptide as defined herein.

A peptide, antigenic substance or precursor thereof as defined herein may be used in diagnosis of RSV infections; or in the prophylaxis of respiratory syncytial virus infections.

This invention also provides a diagnostic testkit for the detection or identification of RSV types or subtypes, or antibodies against RSV types or subtypes, which testkit comprises a peptide, antigenic substance or precursor thereof as defined herein, together with suitable means for detection. The testkit preferably provides for an enzyme linked immunosorbent assay, e.g. a blocking ELISA.

The invention also provides a method for the detection of (antibodies against) RSV comprising contacting a sample of a body fluid with a peptide, antigenic substance or precursor thereof as defined herein, in a manner such that a complex comprising said peptide, antigenic substance or precursor, and an antibody directed against said peptide, substance or precursor can be formed, followed by detection of said complex.

Furthermore, the invention provides a pharmaceutical composition for the prophylaxis of RSV infections comprising a peptide, antigenic substance or precursor thereof as defined herein, together with a suitable adjuvant or excipient for administration to a mammal.

The invention also provides a method for the prophylaxis of RSV infections comprising administering to a mammal a composition as defined above, in an amount sufficient to elicit an immune response against respiratory syncytial virus.

Furthermore, the invention provides a peptidomimeticum which mimics a peptide as defined herein.

Another aspect of this invention is a method for inducing antibodies against RSV types or subtypes comprising administering to a mammalian host an antigenic substance or precursor thereof as defined herein, together with a suitable adjuvant and harvesting resulting antibodies or antibody producing cells from said mammalian host.

An antibody directed against a type or subtype of RSV obtainable by the above method is also part of the invention. Preferably, the antibody is a monoclonal antibody.

In another aspect, the invention provides a diagnostic testkit for the detection of or the discrimination between (antibodies against) subtypes or types of RSV comprising the above antibody and suitable means for detection.

DETAILED DESCRIPTION OF THE INVENTION

Most peptides that have been used in serology represent continuous epitopes. It is impossible to detect antibodies against complex discontinuous epitopes using small linear peptides and it is difficult to predict discontinuous epitopes based on the amino acid sequence of a protein. In addition, the antigenic surface of large globular proteins cannot be mimicked accurately with a small linear peptide. We solved this problem by predicting an independently folding region in the G protein of RSV viruses that adopts a stable tertiary structure while retaining its antigenicity. This prediction is crucial for the correct design of a useful antigen.

RSV-G contains an unusual high amount of hydroxy amino acids which are acceptor sites for O-glycosylation (Johnson et al., 1987). We discovered that hydroxy amino acids like Serine (S) and Threonine (T) are clustered together with Proline (P) in two discrete regions of the G protein of RSV. These regions, enriched in serines, threonines and prolines (STP), are common motifs that are heavily O-glycosylated and probably adopt a stiff and extended conformation (generally reviewed by Jentoft, 1990). Because such regions are the major constituent of mucins (large polymeric molecules that form mucous gels), the regions are called mucin-like regions. By definition, the amino acid sequences in mucin-like regions comprise 25–40% of serine or threonine residues (Jentoft, 1990).

We located the first mucin-like region in RSV-G as extending from the transmembrane region until the conserved double $Pro_{155,156}$ and the second mucin-like region as extending approximately from the conserved $Pro_{194}$ until the C-terminus. We defined the ectodomain of the G protein of RSV as a small hydrophobic globular region which resides between two discrete mucin-like regions. The proposed location of this small central hydrophobic region of RSV-G (FIGS. 1, 2), the possible autonomous folding of this short sequence, its relatively conserved nature, and the sparse potential glycosylation sites therein make a peptide representing this short region a promising candidate to be used as antigen for an immunoassay.

Comparative tests carried out with a peptide essentially corresponding with the 15-residue peptide disclosed by Norrby et al. (the peptide used in said comparative tests was a 16-residue peptide composed of residues 174–189) have shown that a 32-residue peptide corresponding to the central hydrophobic region of HRSV-G reacted better as antigen in an ELISA than said 16-residue peptide which represents only a part of said central hydrophobic region. Probably, the 32-residue peptide adopts a more native-like, complete structure. Tests with a low sensitivity, as obtained when using the 15-residue peptide of Norrby et al., are not suitable for performing sensitive sero-epidemiological studies which is very important when trying to discriminate between types or subtypes of RSV.

The invention provides an antigenic substance for discrimination between individuals Infected with different subtypes of RSV. The antigenic substance is a peptide which corresponds to an amino acid sequence of RSV-G, which is located between the two mucin-like regions.

An antigenic substance according to this invention is to be interpreted as any peptide-like or peptide-based substance capable of inducing an immune response against RSV or recognized by a serum containing antibodies against RSV. Precursors of such antigenic substances are meant to read on comparable peptide-like or peptide-based substances, which are not immunogenic themselves but need for instance to be coupled to a carrier to be able to induce an immune response or to be recognized. Peptide-based or peptide-like substances are intended to include anything with the function of the peptides according to the present invention. This means that these substances may be peptides themselves in which a number of amino acid residues have been replaced or modified. It also means that they may be fusion proteins for instance designed to present the amino acid sequence of the peptides of the invention on their surface. The definition also includes peptidomimetics and anti-idiotype antibodies derived from the peptides according to the invention.

In a preferred embodiment the invention provides peptides that can be used in diagnostic assays for detection of antibodies directed against specific RSV types and subtypes (HRSV and subtypes, BRSV and subtypes, ORSV and subtypes). Furthermore, these peptides can be incorporated in RSV vaccines.

The invention of the independently folding region in the G-protein relates to all types of RSV. As a consequence, the invention is not limited to the peptides specifically disclosed herein, but extends to analogous pep ides and their derivatives in all types of RSV and all subtypes of these viruses.

Preferred peptides to be used according to the invention comprise at least the antigenic parts of the peptides given in table 1 or derivatives thereof, their length being from about 28 residues up to about 37 residues.

We have evaluated the applicability of the peptides in diagnostics by the development of two different diagnostic assays: an indirect ELISA and a blocking ELISA. Both of these tests are type- and subtype-specific.

Other diagnostic assays can of course be easily designed by the man skilled in the art.

These may of course be provided in any suitable format. Assays can be performed in solution on solid phases, they can be performed using any kind of label, such as enzymes, solid particles, such as metal sols, or other sols, latex particles, dyes, fluorescent substances or radioactive materials. They even may be performed without labels, as can be done by agglutination assays. The peptides can be used to detect antibodies in for instance a fluid from a mammal, such as blood, serum, urine, milk. Usually the antibody is bound by a peptide according to the invention, which may be present on a solid phase. Afterwards the complex of peptide and antibody may be detected by a labelled reagent, which can be a labelled antibody directed against human or bovine antibodies.

According to the invention the peptides can also be used to obtain antibodies which are specific for RSV types and/or subtypes. The peptides are administered to a mammal, usually a rodent, in an immunogenic form and after one or more booster administrations the serum from the animal is harvested and antibodies can be purified therefrom. Alternatively, the spleen of such animals may be removed to obtain antibody producing cells. These can be changed, by fusion or transformation, into cell lines producing monoclonal antibodies. Assays based on (monoclonal) antibodies directed to RSV and induced by the peptides according to the invent on are therefore also a part of the invention.

The peptides according to the invention can of course also be used in vaccines to prevent infections with RSV. They may be used in conjunction with other antigens or alone to elicit an immune response against RSV. Usually the peptide has to be coupled to a carrier to be presented in an immunogenic form before administration to a host. Other ways of rendering a peptide sufficiently immunogenic are known to the person skilled in the art. Adjuvants are usually added to vaccines to boost the immune response in a more aspecific manner.

The invention relates to a set of RSV diagnostic assays based on peptides corresponding to the central region of the RSV G protein. The regions are listed in Table 1 for BRSV, ORSV, HRSV-B and HRSV-A. The length of the peptide to be used in a diagnostic assay preferably is from about 28 to about 37 residues (Table 1). The minimal length of a suitable peptide is dictated by the length of the module which lies between $His_{159}$ and $Cys_{186}$. The maximal length of a suitable peptide is dictated by the length of the module which lies between $Pro_{156}$ and $Pro_{194}$.

The region corresponds to a relatively conserved region in a highly variable protein. Between different BRSV strains an amino acid homology of 90% or more is observed, both in the sequences corresponding to the underlined 32-mer peptide shown in Table 1, and in the sequences of the 28-residue module consisting of residues Nos. 159–186. Therefore the invention relates to all peptides listed in Table 1 and all analogous peptides with at most 4 amino acid differences within the 32-mer or within the 28-residue module. Furthermore peptides corresponding to yet to be sequenced subgroups of BRSV or ORSV and their analogues with at most 4 amino acid differences are also part of this invention.

The diagnostic assays based on the peptides can be used to determine antibody levels in blood, serum, milk or other body fluids.

The materials according to the invention can also be used for incorporation in a vaccine.

EXAMPLES

Structure Analysis of RSV Protein G

A detailed analysis of the primary structure of protein G of RSV (RSV-G) allowed a dissection of the protein in shorter modules. In FIG. 1, a schematic presentation is shown based on this analysis of the primary structure. According to this analysis, the protein comprises a cytoplasmic region, a transmembrane region, an elongated mucin-like region (37% Ser and Thr), a central hydrophobic globular region, and a short positively charged region within a second elongated mucin-like region (38% Ser, Thr). The modular architecture demonstrates that the central hydrophobic globular region is positioned between two mucin-like stalks, and limited approximately by an N-terminal conserved double $Pro_{155,156}$ and a C-terminal conserved $Pro_{194}$ (FIGS. 1, 2). This schematic model suggests a very important functional role for the central hydrophobic region in protein binding because it may be the only exposed protein domain.

The rest of the ectodomain of PSV-G is mainly mucin-like. The dense carbohydrate coat of the mucin-like regions is added to the envelope protein by cellular enzyme systems and for that reason the mucin-like regions are probably not very antigenic.

The location of a small hydrophobic protein module between two immunosilent mucin-like regions, the possibly autonomous folding of this short sequence, the relatively conserved nature, and the sparse potential glycosylation sites make a peptide representing this short region a promising candidate to be used as antigen for an immunoassay.

Peptide Synthesis

Peptides were selected from the central hydrophobic region of RSV-G that is located between the two mucin-like regions. The central hydrophobic regions (residues 158–189) of all cloned RSV types and subtypes were synthesized: BRSV-G (Lerch et al., 1990; WO 92/01471); ORSV-G (Mallipeddi and Samal 1993b); HRSV-G type A (Wertz et al., 1985); and HRSV-G type B (Johnson et al., 1987). Additionally, a peptide corresponding to the immunodominant peptide (residues 174–189) of HRSV-G type A was synthesized. BRSV: acetyl-N H Q D H N N F Q T L P Y V P C S T C E G N L A C L S L C H I E-amide (Seq ID No: 5) ORSV: acetyl-I Q Q D Y S D F Q I L P Y V P C N I C E G D S A C L S L C Q D R-amide (Seq ID No: 6) HRSV-A: acetyl-K P N N D F H F E V F N F V P C S I C S N N P T C W A I C K R I-amide (Seq ID No: 8) acetyl-S I C S N N P T C W A I C K R I-amide (Seq ID No: 13) HRSV-B: acetyl-K P K D D Y H F E V F N F V P C S I C N N Q L L K S I C K T I-amide (Seq ID No: 7)

Synthesis of peptides was performed according to standard procedures on an Applied Biosystems 430A synthesizer using Fastmoc chemistry (Fields et al., 1991). Purified oxidized peptide was obtained as follows: β-mercaptoethanol reduced peptide was slowly oxidized by dialysing against 1% $NH_4HCO_3$, which was frequently refreshed, for three days. These peptides were used as antigens in enzyme linked immunosorbent assays (ELISA).

Serum Samples and Monoclonal Antibodies

The following serum samples and monoclonal antibodies were incorporated in the study.

Cattle. Negative field serum samples (N=40) were obtained from 4 to 6 month-old calves which had no detectable antibodies against BRSV for at least one month, using the FELISA (Westenbrink et al., 1985). Sera were collected during the summer season (Van der Poel et al., 1993).

In addition, negative serum samples (N=12) were obtained from specific-pathogen-free SPF) calves. The calves were obtained by caesarean section, deprived of colostrum, and reared in isolation.

BRSV-negative serum samples (N=4), containing antibodies directed against either parainfluenza virus type 3 (PI-3), bovine herpesvirus 1 (BHV1), bovine viral diarrhea virus (BVDV) or mycoplasma, were also incorporated in this investigation.

Field serum samples (N=102) that were positive in the F-ELISA, were obtained from several Dutch farms with a history of BRSV infection (Van der Poel et al., 1993). In the indirect peptide-based ELISA (iG-ELISA), 102 sera were tested and in the blocing peptide-based ELISA (bG-ELISA), 97 of these 102 sera were tested.

Paired serum samples (N=152) from 76 different animals were used to test for increases in antibody titer. Sera were collected with one month interval in December 1990 and in January 1991 at two different Dutch farms (Van der Poel et al., 1993). Some of these sera (N=24) were used to distinguish between reactivity against the BRSV-G peptide or ORSV-G peptide.

Finally, we tested serum samples (N=6) that reacted non-specifically in the F-ELISA.

Sheep. Sheep sera (N=3) positive for RSV in the F-ELISA were obtained from our internal sheep serum bank.

Human. Human sera (N=14), positive for HRSV specific antibodies in a complement fixation test were obtained from Dr. J. A. Melero of the National Centre for Microbiology (Madrid, Spain). These sera were collected from patients, with an age range of 7 months to 70 years, during the 1993–1994 RSV epidemic.

Human sera (N=23) positive for RSV were obtained from Dr. J. C. de Jong of the RIVM in Bilthoven, the Netherlands. These sera were used in the tests to compare the 16-residue with the 32-residue peptide as antigen.

Rabbit. Rabbits (N=3) were immunized with the supernatant of HRSV-A (strain Long) and HRSV-B (strain 9320) infected cells, respectively. Rabbits were vaccinated with 1 ml Freund's complete adjuvant (FCA), mixed 1:1 with 1 ml of supernatant.

Monoclonal antibodies. Production of a BRSV-G specific monoclonal antibody (MAb 20) was performed as described (Wensvoort et al., 1986). Balb/c mice were immunized intraperitoneally with 100 μg BRSV (Lelystad strain), grown on embryonic bovine tracheal cells, mixed with FCA. The RSV-specificity of MAb 20 was determined using an immunoperoxidase monolayer assay (IPMA) as described (Wensvocrt et al., 1986). In this assay Vero cells infected with BRSV (strain Lelystad) were used. Additionally,. MAb 20 reacted in the BRSV-G peptide-based iG- and bG-ELISA.

MAbs 2G and 19G specific for the G protein of HRSV A, were obtained from Dr. J. A. Melero, National Centre for Microbiology (Madrid, Spain). MAbs 26 and 30, specific for the G protein of HRSV B and A, respectively, were a kind gift of Drs. J. Furze and G. Taylor, AFRC Institute for Animal Health, Compton, UK.

Comparison of Antigenicity of Different Peptides

The single linear immunodorrinant region of BRSV-G as determined by peptide binding studies (residues 174–185) and the immunodominant peptide of HRSV-G described by Norrby et al. (residues 174–188) correspond to the C-terminal half of the central hydrophobic region of RSV-G (residues 158–189). To check whether the empirically determined immunodominant epitope of HRSV-G type A (contained within the 16-residue peptide 174–189) has the same antigenic characteristics as the predicted antigenic site (the 32-residue peptide corresponding to the central hydrophobic region 158–189), both peptides were tested for their antigenicity in an iG-ELISA using the G-peptide of HRSV subtype A as antigen. Four times more sera were scored positive in the indirect G-peptide ELISA (iG-ELISA) based on the 32-residue peptide than in the iG-ELISA based on the 16-residue peptide (Table 2). Although the peptide binding studies showed that the immunodominant site is contained in the 16-mer peptide (Norrby et al., 1987), the 32-residue peptide corresponding to the central hydrophobic region of HRSV-G type A as described in this study (FIG. 1) is much more reactive with human sera when compared with the 16-residue peptide. Therefore, 32-residue peptides corresponding to the central hydrophobic region of the G-protein of several types and subtypes of RSV were used as antigen in immuno-assays.

Respirapory Syncytial Virus Specific F-ELISA

Test procedure. The RSV-specific indirect double antibody sandwich assay, used as a routine diagnostic test in our laboratory, was performed essentially as described previously (Westenbrink et al., 1985), except that MAbs, instead of horse anti-RSV serum, were used as capture antibody. In short, microtiter plates coated with two MAbs (No 88953, ID-DLO, Lelystad) directed against BRSV-F were subsequently incubated with bovine RSV antigen, the test serum, rabbit anti-bovine immunoglobulin peroxidase (Dakopatts, P159) and substrate chromogen solution. Before use, and after each incubation step, plates were rinsed six times with deionised water containing 0.05% Tween 80. Dilutions of test sera and reagents were made in "high-salt" ELISA-buffer (8.1 mM $Na_2HPO_4$, 2.79 mM $KH_2PO_4$, 0.8 M NaCl, 2.68 mM KCl, 1 mM EDTA, 0.05% Tween 80, pH 7.2) containing 4% horse serum. BRSV antigen stock solution (No 88915, ID-DLO, Lelystad) was diluted 1:2 (100 ul/well) and incubated during two hours at 37° C. Test sera were diluted 1:80 (100 ul/well) and incubated for one hour at 37° C. Horse-radish peroxidase (HRPO) conjugated rabbit anti-bovine immunoglobulin (Dakopatts, P159) was diluted 1:2000 (100 ul/well) and incubated for one hour at 37° C. The substrate chromogen solution consisted of 10 mM sodium-phosphate buffer (pH 6.8), 0.1 mM EDTA, 0.1% w/v 5-aminosalicylic acid, and freshly added 0.005% v/v H₂O₂. Incubation with substrate solution was performed overnight at 4° C. Colour development was measured at 450 nm (Titertek Multiscan). Absorbance values higher than two times the average background value of testsera in control wells without antigen, were considered positive. Although the test has been developed for the detection of antibodies specific for BRSV, antibodies against all other RSV types can be detected with the test due to extensive F protein immune-crossreactivity between RSV types and subtypes.

Indirect G-peptide ELISA (iG-ELISA)

Test procedure. The iG-ELISA was based on the test procedure of the F-ELISA as described above with the following modifications. The antigen was not caught but directly coated to the plate. One hundred and fifty ng of crude oxidized peptide was coated per well (high binding capacity flat bottom microplate, Greiner) in 100 μl carbonate buffer pH 9.0, 4° C., overnight. The optimal dilution of the peptide to coat the ELISA plates was chosen in such a manner that maximum binding was obtained as determined in a checkerboard titration. Test sera, diluted 1:5, and conjugate were incubated for one hour at 37° C. in "low-salt" ELISA buffer (8.1 mM Na$_2$HPO$_4$, 2.79 mM KH$_2$PO$_4$, 0.5 M NaCl, 2.68 mM KCl, 1 mM Na$_2$EDTA, 0.05% v/v Tween 80, pH 7.2) containing 4% horse serum. Subsequently, the test was performed as described above. The conjugates used in the test were anti-bovine (1:2000), anti-sheep (1:1000), and anti-human HRPO (1:1000) (Dakopatts). Absorbance values higher than two times the average background value of testsera in control wells without antigen, were considered positive.

iG-ELISA

The reactivity of different panels of bovine sera in the iG-ELISA was compared with the reactivity in a routine diagnostic F-ELISA (FIG. 3). By using the mean OD of all negative sera (N=40) plus twice the standard deviation ($\chi$+2SD=0.062) as cut-off value for negativity, the relative specificity of the iG-ELISA was found to be 0.98. Using this cut-off value, the sensitivity of the test was determined using 102 positive field serum samples from several Dutch farms and was found to be 0.90 (92/102). Four different sera containing antibodies against other microorganisms (BHV1, BVDV, PI-3, mycoplasma) were all negative in the iG-ELISA (data not shown). Six sera that reacted non-specifically in the routine F-ELISA reacted also non-specifically in the iG-ELISA (data not shown).

The low sensitivity compared to the routine F-ELISA may be due to (i) a relative low antigenicity of BRSV-G in comparison to that of BRSV-F, (ii) low antibody titers of some animals, or (iii) some sera may be directed to another, yet uncharacterized, subtype.

Blocking G-peptide ELISA (bG-ELISA)

Test procedure. This ELISA for measuring BRSV-specific antibodies is based on blocking of the interaction of a BRSV-G specific monoclonal antibody (MAb 20) with the coated peptide by peptide-specific antibodies that may be present in the test sample. ELISA plates were coated with 30 ng crude oxidized peptide per well in 100 μl carbonate buffer pH 9.0, 4° C., overnight. The optimal dilution of the peptide to coat the ELISA plates was chosen in such a manner that a near maximum binding was obtained as determined in a checkerboard titration and that the sensitivity of the test was maintained high. Before use, and after each incubation step, plates were rinsed six times with deionised water containing 0.05% Tween 80. Plates were subsequently incubated with test serum diluted 1:2, a HRPO-conjugated monoclonal antibody specific for the G-peptide (bovine RSV-MAb 20, ID-DLO, Lelystad) diluted 1:5000, and substrate chromogen solution. Incubation with substrate solution was performed overnight at 4° C. Test sera and conjugate were incubated for one hour at 37° C. in "low-salt" ELISA buffer containing 4% horse serum.

Blocking percentages of each test sample was calculated by using the optical density at 450 nm of "low salt" ELISA buffer containing 4% horse serum as reference (=0% blocking) according to the following formula:

blocking percentage of test sample =

$$\frac{OD(\text{"low salt" buffer}+\text{horse serum}) - OD(\text{test sample})}{OD(\text{"low salt" buffer}+\text{horse serum})} \times 100\%$$

bG-ELISA

Blocking percentages of different panels of bovine sera were compared in the bG-ELISA (FIG. 4). When the mean blocking percentage of all negative sera (N=40) ($\chi$+2SD=42%) was used as cut-off value for negativity, the relative specificity was found to be 0.98. The relative sensitivity of the test as determined using 97 of the 102 positive field serum samples, was found to be 0.98 (95/97). Sera containing antibodies against other microorganisms (BHV-1, BVDV, PI-3, mycoplasma) were all negative in the bG-ELISA (data not shown). The six sera that reacted non-specifically in the routine F-ELISA and in the iG-ELISA, were tested in the bG-ELISA. One of these sera blocked significantly (75%), suggesting that this serum was positive for BRSV antibodies.

Detection of RSV Infection

An antibody titer rise (≧4x) in paired sera is normally regarded as being the result of an infection or reinfection. In 76 paired serum samples, seroconversion or at least a fourfold titer rise was detected 42 times in the iG-ELISA and 32 times in the routine F-ELISA (Table 3). The difference in frequency of titer rise seems to be related to the age of the animals (Table 3). The BRSV IG-ELISA was more sensitive in detecting reinfections than the F-ELISA. The difference in frequency of titer increases seemed to be associated with the age of the animal. The iG-ELISA and the routine F-ELISA were equally sensitive for detection of seroconversion in young calves (age<1 year). However, in older cattle (age more than 1 year), antibody titer increases were detected more frequently when the iG-ELISA was used. Therefore, the number of reinfections may be underestimated when titer increases are based on the F-ELISA. The different results of both assays may be explained by (i) a faster drop of antibody titers against G compared with that of F after infection, or (ii) by the lower antibody response against G as compared to that against F after the first infection. Consequently, a reinfection may induce a more pronounced increase in antibodies against G than against F. Therefore, G-specific ELISAs, including the peptide ELISAs described in this patent, may have the advantage over ELISAs based on the F protein, that they better detect reinfections with RSV.

Type- and Subtype-specificity of Peptide-ELISA

RSV ELISAs based on whole virus contain antigenic proteins which are very conserved. Therefore, such ELISAs are not type- or subtype-specific, which means that these assays do not distinguish between human RSV and ungulate RSV, and certainly not between HRSV-A and HRSV-B or between BRSV and ORSV. A dendogram was calculated based on the phylogenetic relationship of RSV according to the amino acid sequence of RSV-G and on the central hydrophobic region of PSV-G (FIG. 5). Because RSV-G is highly variable between RSV types and subtypes, we investigated whether peptide-based iG-ELISAs were able to recognize type-, or subtype-specific antibodies. The reactivity of 14 sera of patients collected during the 1993–1994 epidemic in Madrid showed that 13 sera reacted specifically in the HRSV iG-ELISA and not in the BRSV iG-ELISA (Table 4). Furthermore, 12 sera had a higher reactivity in the HRSV-A iG-ELISA than in the HRSV-B iG-ELISA. Polyclonal rabbit sera directed against HRSV-A or HRSV-B were tested for their reactivity against the HRSV peptides. Table 5 shows that sera of rabbits immunized with HRSV-A reacted only in the HRSV-A iG-ELISA, and the serum of the rabbit immunized with HRSV-B reacted only in the HRSV-B iG-ELISA. Furthermore, four G-specific MAbs with known subtype-specificity tested in the iG-ELISA did not show cross-reactivity (Table 4). Previous studies confirmed the subtype-specificity of an ELISA based on the 15-residue peptide using some paired serum samples (Åkerlind-Stopner et al., 1990, Norrby et al., 1987).

ORSV and BRSV are two ungulate RSV types which are genetically equally distant compared to the distance between HRSV subtype A and HRSV subtype B (FIG. 5). The genetic distance based on the amino acid sequence of the central hydrophobic region is slightly longer between ORSV and BRSV than between HRSV-A and HRSV-B. Therefore, the subtype-specificity of the RSV iG-ELISA can also be checked with RSV10 positive sera of sheep and cattle, which most likely can only be infected with ORSV and BRSV, respectively. Bovine sera of 24 different animals, collected at the same timepoint, and reacting positively in the routine F-ELISA, were tested for reactivity in the BRSV iG-ELISA and the ORSV IG-ELISA, respectively (Table 5). The bovine sera reacted in the BRSV iG-ELISA and not in the ORSV iG-ELISA. In addition, three RSV-positive ovine sera reacted only in the ORSV iG-ELISA and not in the BRSV iG-ELISA (Table 5).

Vaccine Study

Two peptide vaccines were used to test the immunogenicity of the peptide in calves and to examine whether vaccination with the peptide could reduce or inhibit virus infection. One calf was vaccinated once with the 32-residue BRSV-G peptide in Freund's complete adjuvant (FCA), one calf was vaccinated once with the 32-residue BRSV-G peptide coupled to Keyhole Limpet Haemocyanin (KLH) in FCA, and a control calf was not vaccinated. Antibody reactivity against the peptide was monitored during the experiment (FIG. 6). Nine weeks after the vaccination the animals were challenged nassally with 2 ml virus (Odijk strain, TCID50: $10^{3.8}$/ml) . Before challenge, and 5, 7, 11 and 14 days after challenge lung washings were taken from the calves. Cells in the washings were tested for the presence of BRSV antigen, and virus titrations were performed with the washings (FIGS. 7a,b). The calf vaccinated with the peptide conjugated to the carrier protein shows a considerate protection against virus challenge. The protection is better for the conjugated peptide compared with the unconjugated, which seems to be associated with the antibody response against the peptide (FIGS. 6, 7).

Figure 1:
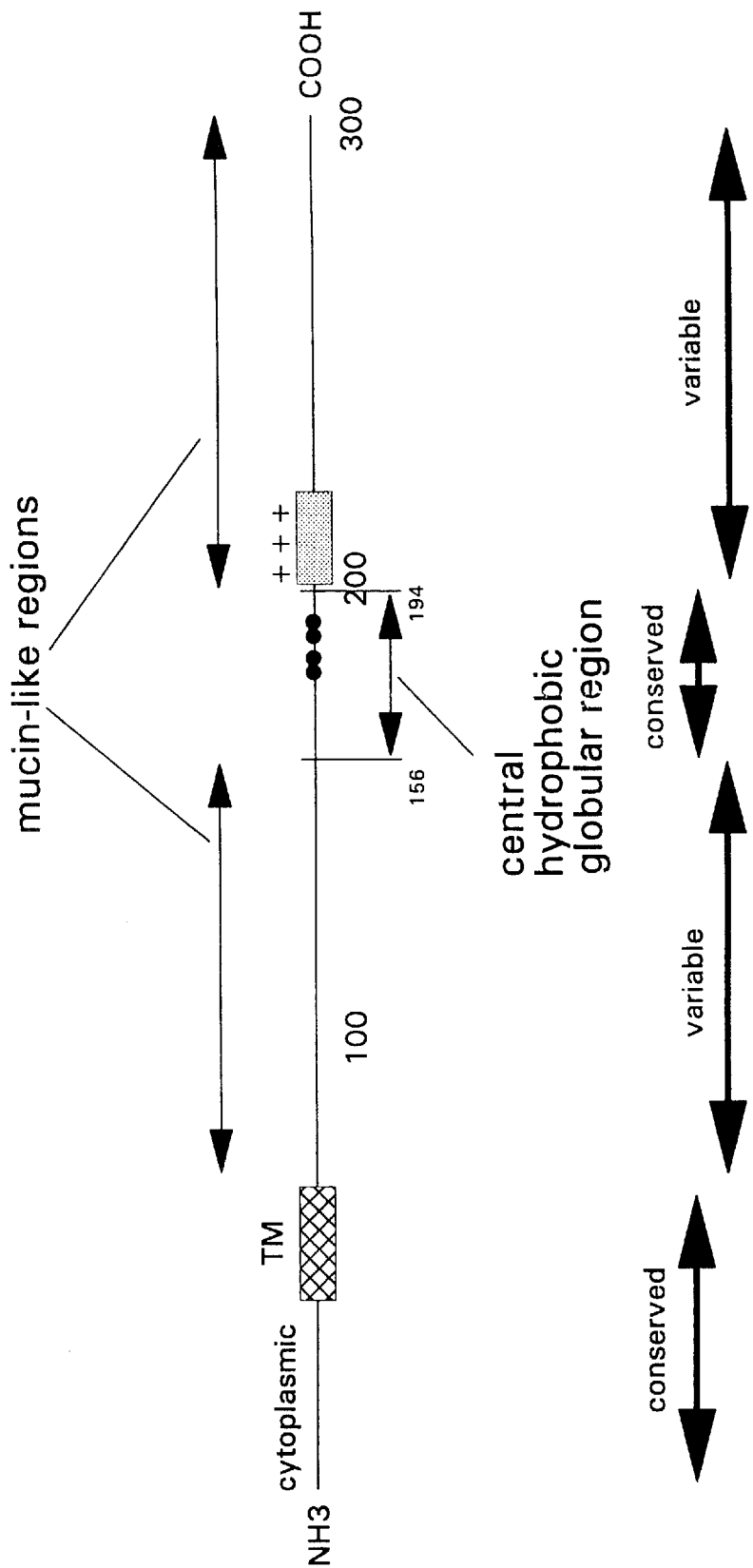
FIG. 1.
Figure 2:
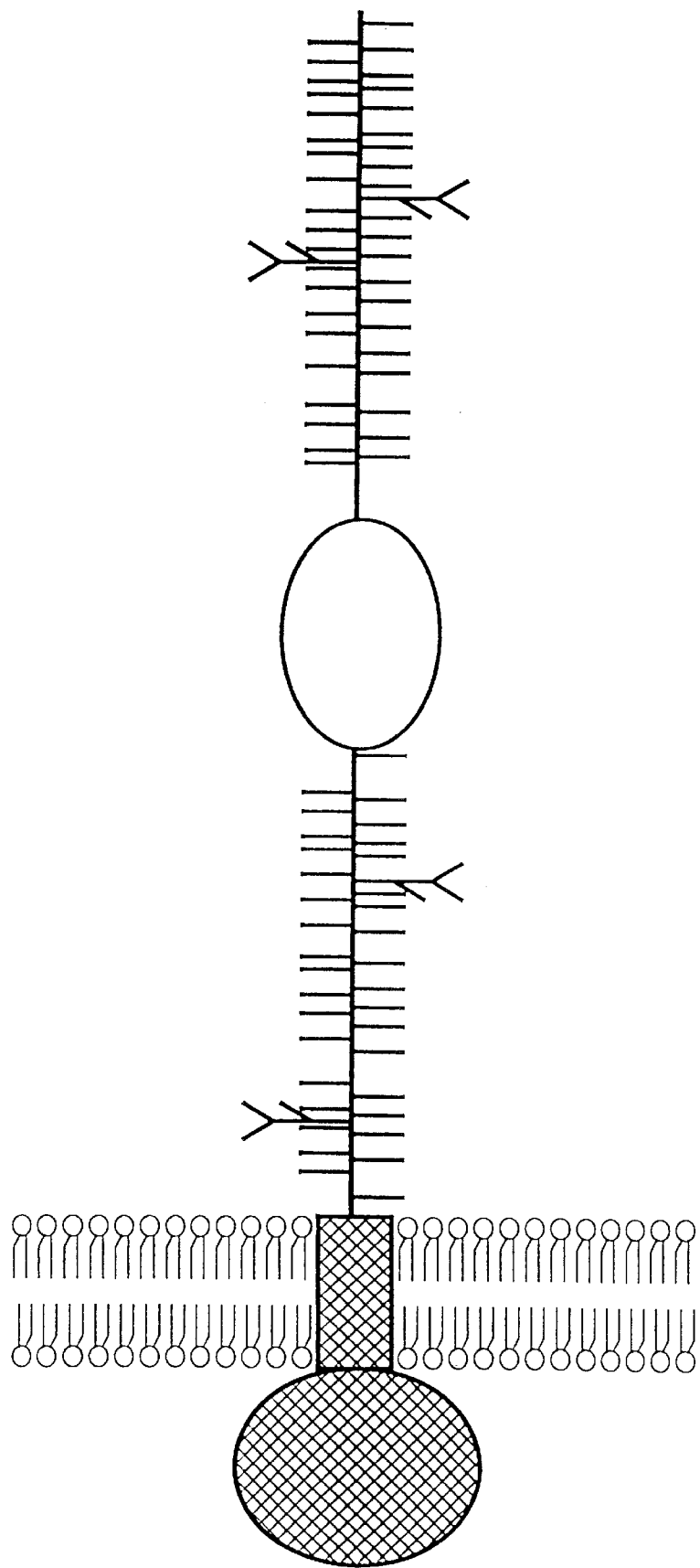
Figure 3A:
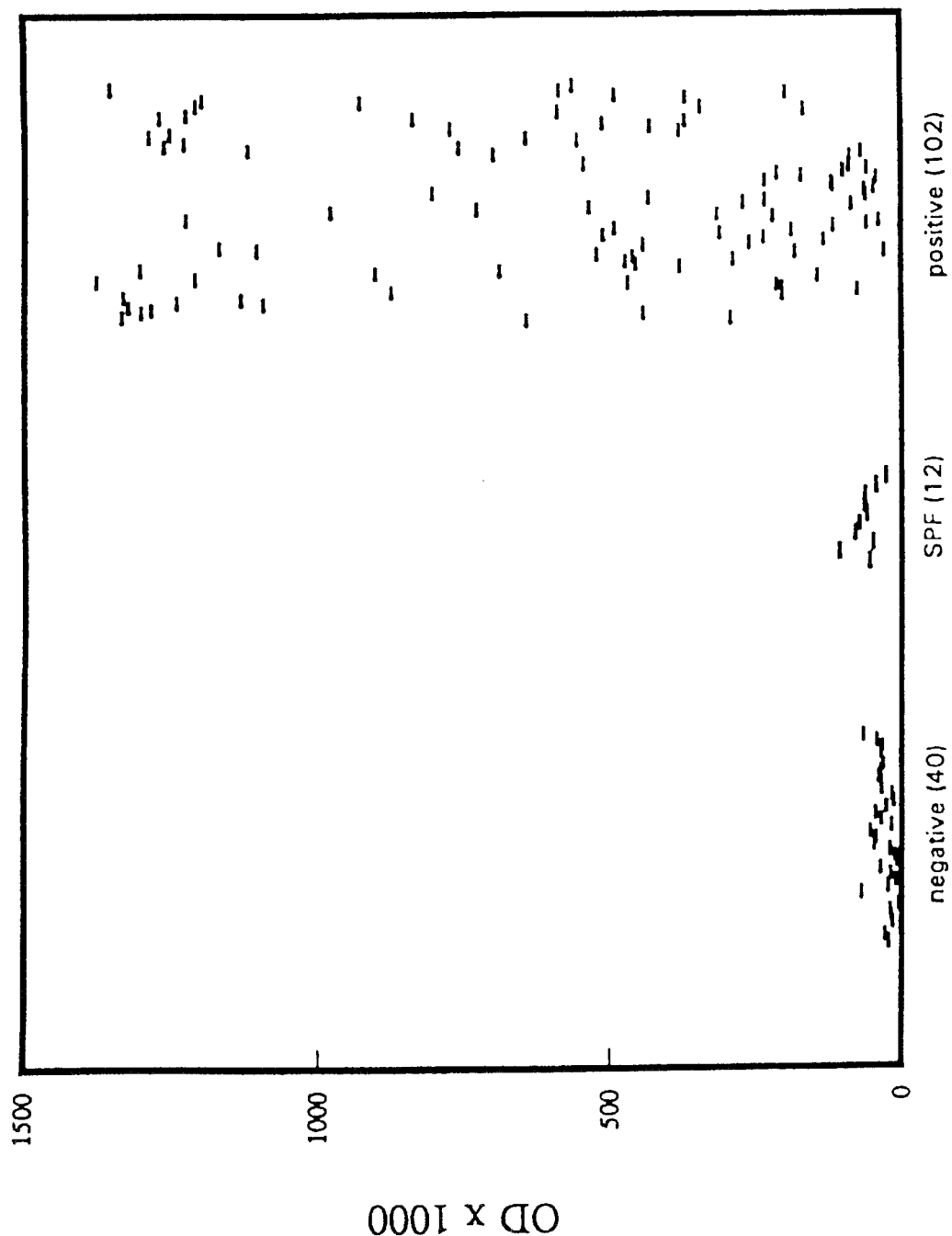
Figure 3B:
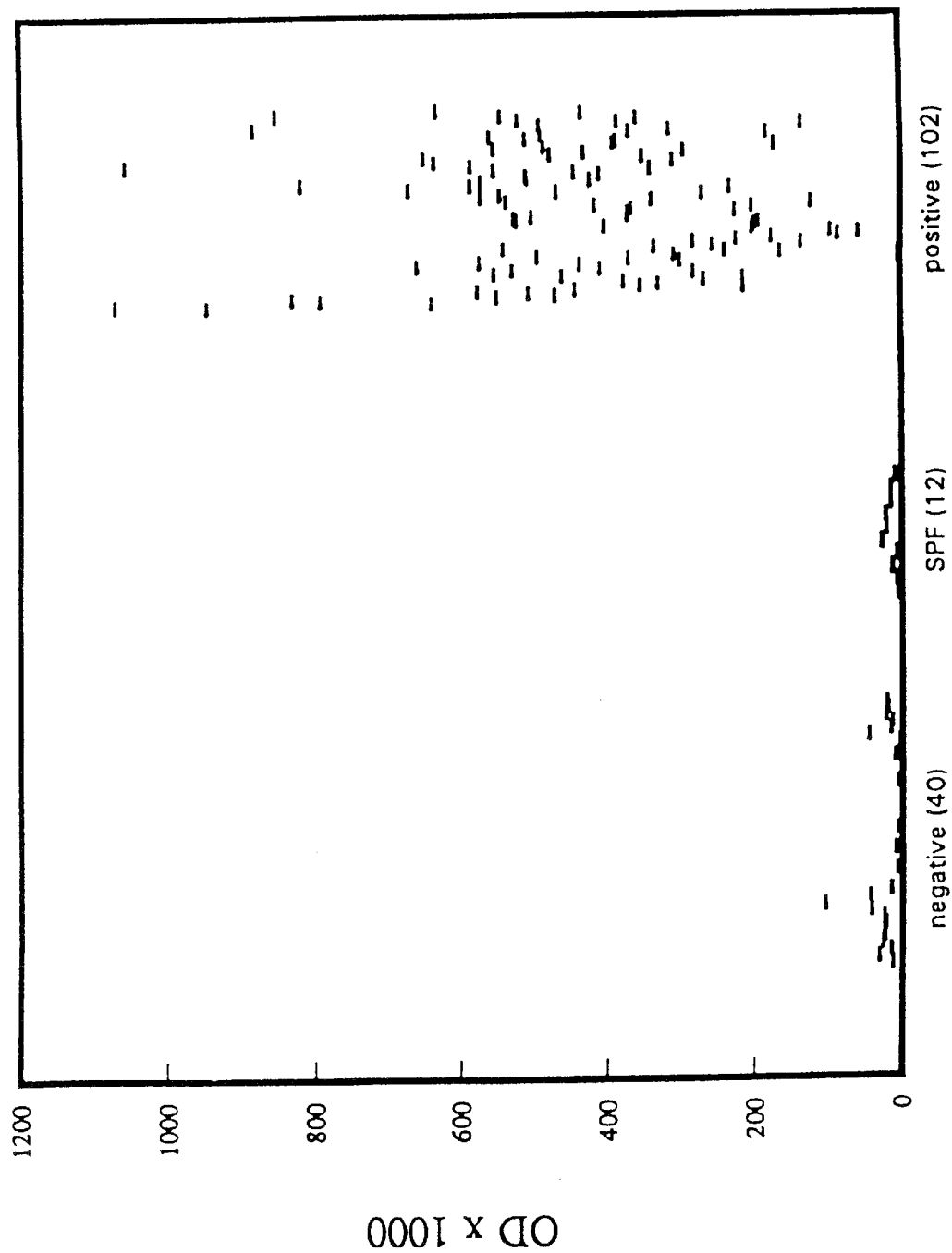
Figure 4:
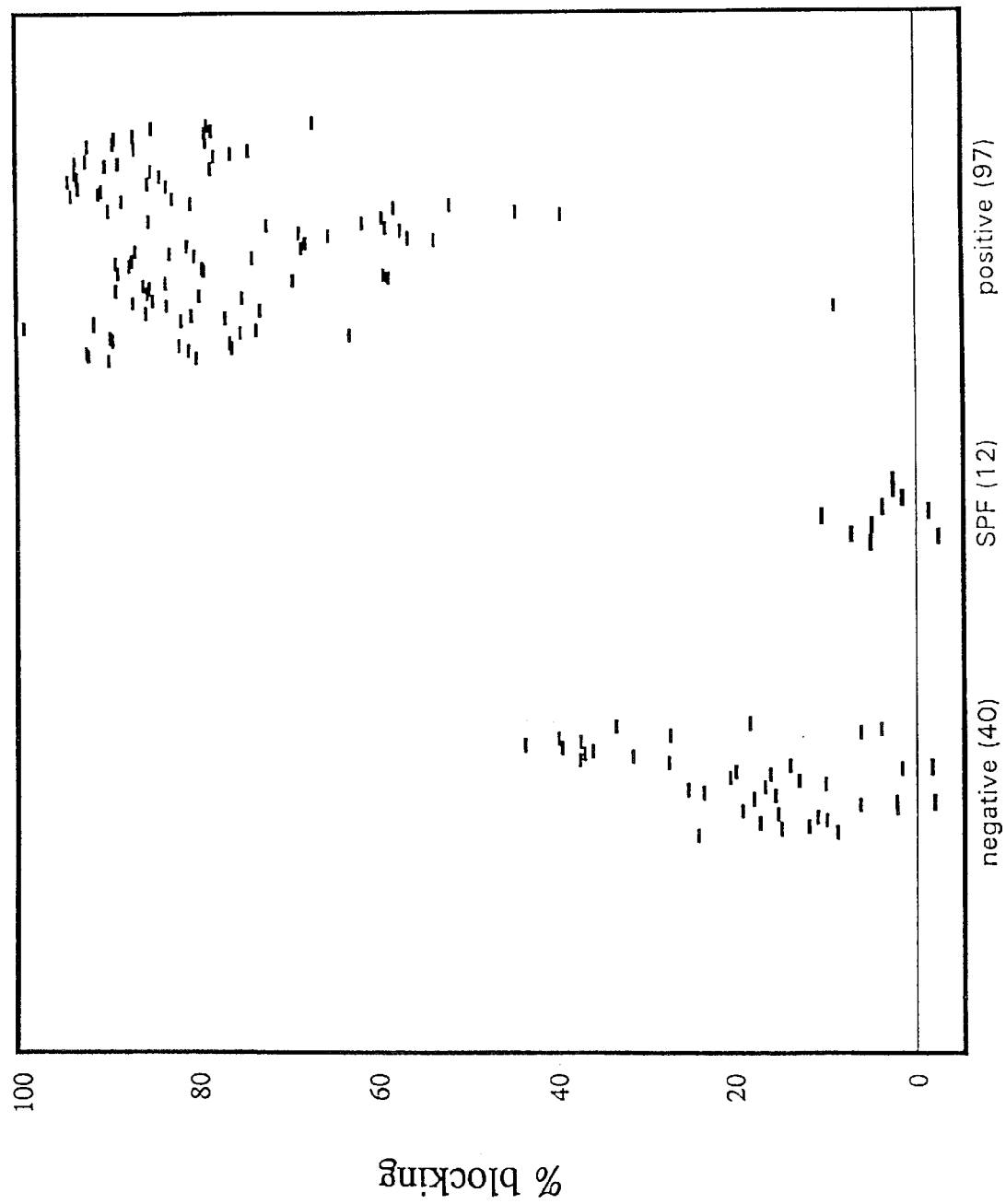
Figure 6:
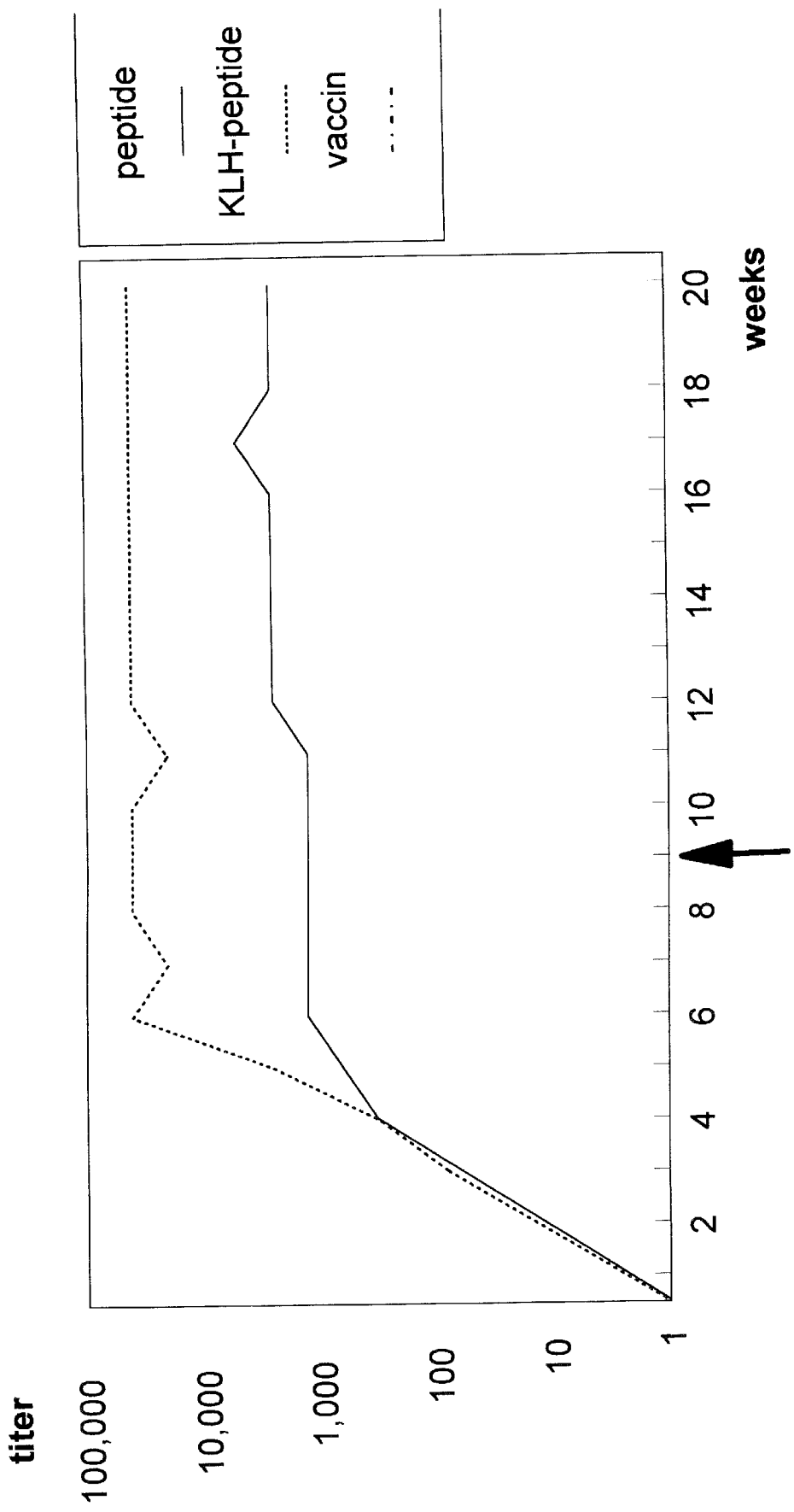
Figure 7A:
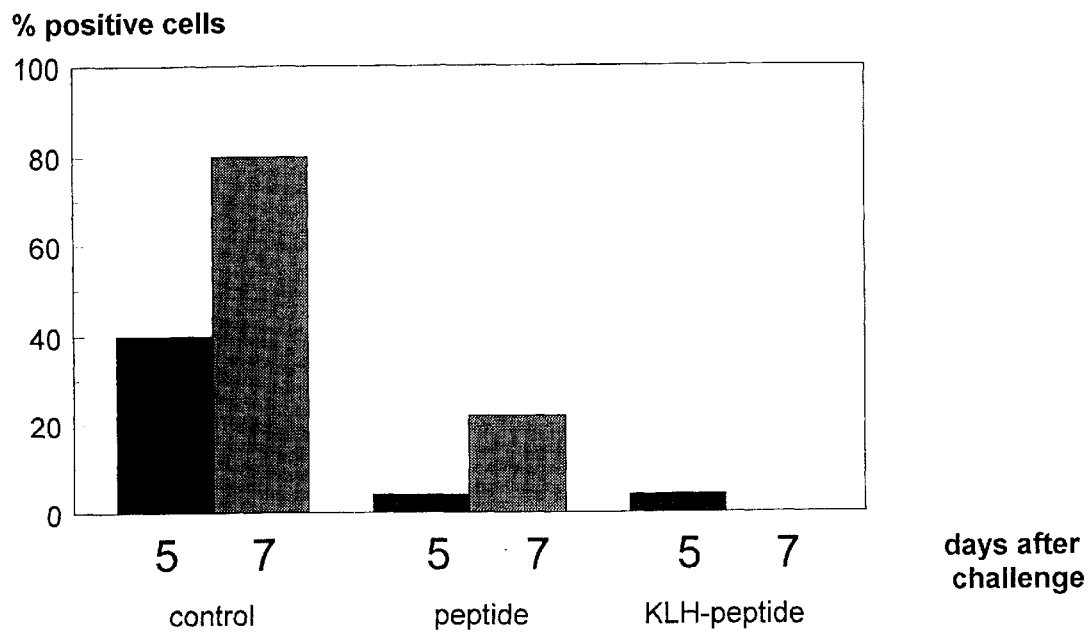
Figure 7B:
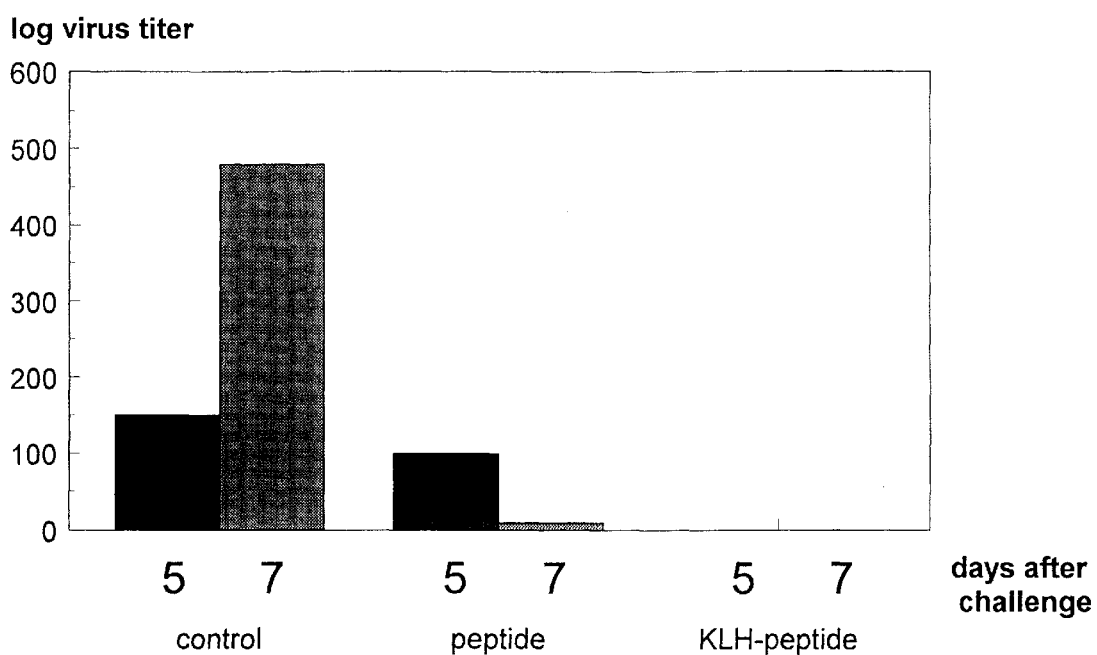

a schematic representation of the primary structure of RSV-G; Hatched box: transmembrane region (TM); dotted box: positively charged region. The extent of the mucin-like regions is indicated by upper arrows, which corresponds with a high content of serine, threonine and proline (37–38% serine and threonine content). •=cysteine. The bottom of the figure displays the general variablility in G (Sullender et al., 1991, Cane et al., 1991, Mallipeddi and Samal, 1993a).

FIG. 2:

Schematic structural model of RSV-G. The central hydrophobic region (residues 158–189) is shown as a grey ellipse. Mucin-like regions are shown with potential O-linked glycosylation sites (short horizontal lines) and potential N-linked glycosylation sites (branched lines). Hatched regions correspond to the transmembrane region and the cytoplasmic region.

FIG. 3:

a. Reactivity of different sera in the BRSV iG-ELISA as described in the test procedure.

b. Reactivity of different sera in the BRSV F-ELISA as described in the test procedure.

FIG. 4:

Blocking percentages of different sera in the BRSV bG-ELISA as described in the test procedure. Note that some negative sera have blocking percentages below zero.

FIG. 5:

Amino acid distances between (a) RSV-G proteins, and (b) central hydrophobic regions of RSV-G (residues 158–189). Phylogenetic analysis was performed with the neighbour-joining method (Saitou and Nei, 1987) and the UPGMA method of clustering in the PHYLIP package (Felsenstein, 1989).

FIG. 6:

Reciprocal of antibody dilution positive for the BRSV iG-ELISA. Numbers on the x-axis indicate the number of weeks after vaccination. The arrow indicates the time of challenge.

FIG. 7:

a: Percentage of positive cells in lung washing of two vaccinated and one unvaccinated calf on day 5 and day 7 after challenge. Cells were stained using a BRSV-F specific MAb conjugated with fluoresceine.

b: Virus titer in lung washing.

REFERENCES

Åkerlind-Stopner B., G. Utter, M. A. Mufson, C. Orvell, R. A. Lerner, and E. Norrby (1990). Subgroup-Specific Antigenic Site in the G Protein of Respiratory Syncytial Virus Forms a Disulfide-Bonded Loop. *J. of Vir.* 64, 5143–5148.

Cane P. A., D. A. Matthews and C. R. Pringle (1991). Identification of variable domains of the attachment (G) protein of subgroup A respiratory syncytial viruses. *J. of Gen. Vir.* 72, 2091–2096.

Edwards J. A. (1989). The effect of stressors like rumen overload and induced abortion on BRD in feedlot cattle. *Agri-Practice* 10, 10–15.

Felsenstein J. (1989). PHYLIP, Phylogeny Inference Package (Version 3.2). *Cladistics* 5, 164–166.

Fields C. G., D. H. Lloyd, R. L. Macdonald, K. M. Ottenson, and R. L. Noble. (1991). HBTU activation for automated Fmoc solid-phase peptide synthesis. *Pept. Res.* 4, 95–101.

Furze J., G. Wertz, R. Lerch, and G. Taylor (1994). Antigenic heterogeneity of the attachment protein of bovine respiratory syncytial virus. *J. Gen. Virol.* 75, 363–370.

Healy A. M., M. L. Monaghan, H. F. Basset, H. M. Gunn, B. K. Markey, and J. D. Collins (1993). Morbidity an mortality in a large Irish feedlot; microbiological and serological findings in cattle with acute respiratory disease. *Br. Vet.J.* 149, 549–560.

Jentoft N. (1990). Why are proteins O-glycosylated? *TIBS* 15, 291–294.

Johnson P. R., M. K. Spriggs, R. A. Olmsted and P. L. Collins (1987). The G glycoprotein of human respiratory syncytial viruses of subgroups A and B: E:.:tens-ve sequence divergence between antigenically related proteins. *Proc. Natl. Acad. Sci. USA* 84, 5625–5629.

Lerch R. A., K. Anderson and G. W. Wertz (1990). Nucleotide sequence analysis and expression from recombinant vectors demonstrate that the attachment protein G of bovine respiratory syncytial virus is distinct from that of human respiratory syncytial virus. *J. of Vir.* 64, 5559–5569.

Mallipeddi S. K. and S. K. Samal (1993a). Sequence variability of the glycoprotein gene of bovine respiratory syncytial virus. *J. of Gen. Vir.* 74, 2001–2004.

Mallipeddi S. K. and S. K. Samal (1993b). Analysis of the ovine respiratory syncytial virus (RSV) G glycoprotein gene defines a subgroup of ungulate RSV. *J. of Gen. Vir.* 74, 2787–2791.

Norrby E., M. A. Mufson, H. Alexander, R. A. Houghten and R. A. Lerner (1987). Site-directed serology with synthetic peptides representing the large glycoprotein G of respiratory syncytial virus. *Proc. Natl. Acad. Sci. USA*. 84, 6572–6576.

Saitou N. and M. Nei (1987). The neighbor-joining method: a new method for reconstructing phylogenetic trees. *Mol. Biol. Evol.* 4, 406–425.

Satake M., J. E. Coligan, N. Elango, E. Norrby and S. Venkatesan (1985). Respiratory syncytial virus envelope glycoprotein (G) has a novel structure. *Nucleic Acids Res.* 13, 7795–7812.

Stott E. J. and G. Taylor (1985). Respiratory syncytial virus: brief review. *Arch. Virol.* 84, 1–52.

Sullender W. M., M. A. Mufson, L. J. Anderson and G. W. Wertz (1991). Genetic diversity of the attachment protein of subgroup B respiratory syncytial viruses. *J. Virol.* 65, 5425–5434.

Van der Poel W. H. M., J. A. Kramps, W. G. J. Middel, J. T. van Oirschot and A. Brand (1993). Dynamics of bovine respiratory syncytial virus infections: a longitudinal epidemiological study in dairy herds. *Arch. Virol.* 133, 309–321.

Welliver R. C. (1988). Detection, pathogenesis and therapy of respiratory syncytial virus infections. *Clin. Microbiol. Rev.* 1, 27–39.

Wensvoort G., C. Terpstra, J. Boonstra, M. Bloemraad and D. van Zaane. 1986. Production of monoclonal antibodies against swine fever virus and their use in laboratory diagnosis. *Vet. Microbiol.* 12, 101–108.

Wertz G. W., P. L. Collins, Y. Huang, C. Gruber, S. Levine and L. A. Ball (1985). Nucleotide sequence of the G protein of human respiratory syncytial virus reveals an unusual type of viral membrane protein. *Proc. Natl. Acad. Sci. USA*. 82, 4075–4079.

Westenbrink F., J. M. A. Brinkhof, P. J. Straver, J. Quak and P. W. de Leeuw (1985). Comparison of a newly developed enzyme-linked immunosorbent assay with complement fixation and neutralisat ion tests for serology of bovine respiratory virus infections. *Res. Vet. Sci.* 38, 334–340.

TABLE 1

Peptide sequences corresponding to the central region of RSV-G*

| | | |
|---|---|---|
| BRSV | (SEQ ID NO:9) | E N H Q D H N N F Q T L P Y V P C S T C E G N L A C L S L C H I E T E |
| ORSV | (SEQ ID NO:10) | E I Q Q D Y S D F Q I L P Y V P C N I C E G D S A C L S L C Q D R S E |
| HRSV-B | (SEQ ID NO:11) | K K P K D D Y H F E V F N F V P C S I C G N N Q L C K S I C K T I P S |
| HRSV-A | (SEQ ID NO:12) | N K P N N D F H F E V F N F V P C [S I C S N N P T C W A I C K R] I P N |

*Box in HRSV-A sequence is immunodominant antigenic site according to empirical study of Norrby et al. (1987). Residues underlined by a broken line correspond to 32-mer peptides which are used in our study. Sequences were taken from Lerch et al. (1990) for BRSV, Mallipeddi and Samal (1993b) for ORSV, Johnson et al. (1987) for HRSV-B and Wertz et al. (1985) for HRSV-A.

TABLE 2

Reactivity of human sera (N = 23) in the iG-ELISA based on the 16- or 32-residue peptide[a].

| | Reactivity | |
|---|---|---|
| Peptide | + | − |
| 16-mer | 3 | 20 |
| 32-mer | 12 | 11 |

[a]Peptides corresponding to HRSV-A G-protein as described in the test procedure.
Sera were diluted 1:25.

TABLE 3

Frequency of rise in antibody titer (≧4x), or seroconversion of paired bovine sera in different ELISAs.

| Farm | (No. of animals) | Frequency for different ELISAs | |
|---|---|---|---|
| | | iG-ELISA | F-ELISA |
| 1 | (N = 24) | 13/24 | 9/24 |
| 16, age < 1 year | (N = 26) | 17/26 | 18/26 |
| age > 1 year | (N = 26) | 12/26 | 4/26 |
| total | (N = 76) | 42/76 | 31/76 |

TABLE 4

Reactivity of human sera in the F-ELISA and the iG-ELISAs[a].

| | RSV-F ELISA | iG-ELISA HRSV-A | iG-ELISA HRSV-B | iG-ELISA BRSV |
|---|---|---|---|---|
| human serum (epidemic '94 Madrid) | | | | |
| 487 | >160 | 10 | <5 | <5 |
| 2369 | >160 | 640 | 20 | <5 |

TABLE 4-continued

Reactivity of human sera in the F-ELISA and the iG-ELISAs[a].

| | RSV-F ELISA | iG-ELISA HRSV-A | iG-ELISA HRSV-B | iG-ELISA BRSV |
|---|---|---|---|---|
| 2219 | >160 | 320 | 80 | <5 |
| 1740 | >160 | 10 | 5 | <5 |
| 1484 | >160 | 80 | <5 | <5 |
| 2377 | >160 | 10 | 5 | <5 |
| 2387 | >160 | 40 | 10 | <5 |
| 1092 | >160 | 20 | <5 | <5 |
| 420 | >169 | 20 | <5 | <5 |
| 199 | <20 | <5 | <5 | <5 |
| 2319 | >160 | 10 | 5 | <5 |
| 455 | >160 | 20 | 20 | <5 |
| 483 | >160 | 40 | <5 | <5 |
| 453 | >160 | 20 | <5 | <5 |
| rabbit serum | | | | |
| 126 | A | N.T[b] | 320 | <5 | N.T |
| 127 | A | N.T | 320 | <5 | N.T |
| 128 | B | N.T | <5 | 40 | N.T |
| MAbs | subtype | | | |
| 2 G | A | N.T | 1250 | <100 | <100 |
| 19 G | A | N.T | 2000 | <100 | <100 |
| 30 | A | N.T | 6000 | <100 | <100 |
| 26 | B | N.T | <100 | 800 | <100 |

[a]Sera were two-fold diluted, starting with a 1:5 dilution for polyclonal sera and 1:100 for MAbs.
[b]N.T = not tested.

TABLE 5

Reactivity of bovine and ovine sera in the iG-ELISAs based on the BRSV-G peptide or the ORSV-G peptide.

| serum | BRSV G | ORSV G |
|---|---|---|
| 1 | 10 | <5 |
| 2 | 5 | <5 |
| 3 | 10 | <5 |
| 4 | >40 | <5 |
| 5 | >40 | <5 |
| 6 | >40 | <5 |
| 7 | >40 | <5 |
| 8 | >40 | <5 |
| 9 | >40 | <5 |
| 10 | >40 | <5 |
| 11 | >40 | <5 |
| 12 | 5 | <5 |
| 13 | >40 | <5 |
| 14 | >40 | <5 |
| 15 | >40 | <5 |
| 16 | 5 | <5 |
| 17 | >40 | <5 |
| 18 | 5 | <5 |
| 19 | >40 | <5 |
| 20 | 5 | <5 |
| 21 | 5 | <5 |
| 22 | >40 | <5 |
| 23 | >40 | <5 |
| 24 | >40 | <5 |
| sheep 1 | <5 | 40 |
| sheep 2 | <5 | 10 |
| sheep 3 | <5 | 40 |

I claim:

1. A peptide of 28 to 37 amino acids having the sequence of a region of protein G of a respiratory syncytial virus (RSV), wherein said region is an independently folding globular protein module which is located between two mucin-like regions in the G protein.

2. The peptide of claim 1, wherein the RSV is selected from the group consisting of bovine RSV, human RSV A, human RSV B, and ovine RSV.

3. The peptide of claim 1, which has the sequence of bovine RSV, human RSV A, human RSV B, or ovine RSV that corresponds to residues 159–186 of bovine RSV protein G.

4. The peptide of claim 1, which has the sequence of bovine RSV, human RSV A, human RSV B, or ovine RSV that corresponds to residues 158–189 of bovine RSV protein G.

5. The peptide of claim 1, which has the amino acid sequence of residues 157–193 of bovine RSV protein G.

6. The peptide of claim 1, wherein the sequence comprises SEQ ID NO 1, SEQ ID NO 2, SEQ ID NO 3, or SEQ ID NO 4.

7. The peptide of claim 1, wherein the sequence comprises SEQ ID NO 5, SEQ ID NO 6, SEQ ID NO 7, or SEQ ID NO 8.

8. The peptide of claim 1, wherein the sequence is SEQ ID NO 9, SEQ ID NO 10, SEQ ID NO 11, or SEQ ID NO 12.

9. An antigenic substance which is a fusion protein comprising the sequence of the peptide of claim 1 fused to a foreign sequence, or a conjugate comprising the peptide of claim 1, linked to a carrier.

10. A diagnostic test kit for detecting or identifying RSV types or subtypes, comprising the peptide of claim 1 or the antigenic substance of claim 9, and ingredients for detecting complex formation.

11. The test kit of claim 10, further comprising an antibody that binds G protein of at least one RSV type or subtype.

12. The test kit of claim 10, wherein the ingredients for detecting are ingredients for an enzyme-linked immunosorbent assay.

13. A method for detecting antibodies against RSV, comprising contacting a sample of a body fluid with the peptide of claim 1 or the antigenic substance of claim 9 in a manner allowing formation of a complex between said peptide or substance and said antibodies, and detecting said complex.

14. An immunogenic composition for administration to a mammal, comprising an immunogenically effective amount of the peptide of claim 1 or the substance of claim 9, together with an adjuvant or excipient.

15. A method of inducing an immune response against respiratory syncytial virus, comprising administering to a mammal the composition of claim 14.

16. A method of prophylaxis of respiratory syncytial virus infection, comprising administering to a mammal a prophylactically effective amount of the composition of claim 14.

17. A method for inducing antibodies against RSV types or subtypes comprising administering the composition of claim 14, and harvesting antibodies that will bind the peptide or antigenic substance.

18. An isolated antibody directed against the peptide of claim 1.

19. The antibody of claim 18, which is a monoclonal antibody.

20. A polyclonal antiserum made by the method of claim 17.

21. A diagnostic test kit for detecting or discriminating between types or subtypes of RSV, comprising the antibody of claim 18 or the antiserum of claim 20, and ingredients for detecting complex formation.

22. A method of detecting RSV, comprising contacting a body fluid with the antibody of claim 18 or the antiserum of claim 20 in a manner allowing formation of a complex between said RSV and said antibody or antiserum, and detecting said complex.

* * * * *

UNITED STATES PATENT AND TRADEMARK OFFICE
CERTIFICATE OF CORRECTION

PATENT NO.    : 6,077,511
DATED         : June 20, 2000
INVENTOR(S)   : Langedijk It is certified that error appears in the above-identified patent and that said Letters Patent is hereby corrected as shown below:

Title page, Item [54] and Column 1, line 1,
Change "PEPTIDE" to -- PEPTIDES --; and Item [57], ABSTRACT,
Line 4, change "andgenic" to -- antigenic --.

Column 1,
Line 51, after "subgroup(s)" insert -- . --;

Column 4,
Line 52, change "Infected" to -- infected --;

Column 5,
Line 17, change "pep ides" to -- peptides --;
Line 54, change "invent on" to -- invention --;

Column 6,
Line 46, change "PSV-G" to -- RSV-G --;

Column 7,
Line 2, after "No: 5)" insert -- ; --;
Line 3, after "No: 6)" insert -- ; --;
Line 5, after "No: 8)" insert -- ; --;
Line 6, after "No: 13)" insert -- ; --;
Line 8, change "C N N" to -- G N N --; change "L L K" to -- L C K --; and after "No: 7)" insert -- . --;
Line 23, change "FELISA" to -- F-ELISA --;
Line 27, change "SPF)" to -- (SPF) --;
Line 39, change "blocing" to -- blocking --;

UNITED STATES PATENT AND TRADEMARK OFFICE
CERTIFICATE OF CORRECTION

PATENT NO.    : 6,077,511
DATED         : June 20, 2000
INVENTOR(S)   : Langedijk It is certified that error appears in the above-identified patent and that said Letters Patent is hereby corrected as shown below:

Column 8,
Line 6, change "(Wensvocrt" to -- (Wensvoort --;
Line 7, change "Additionally,." to -- Additionally, --;
Line 17, change "immunodorrinant" to -- immunodominant --;

Column 10,
Line 65, change "PSV-G" to -- RSV-G --;

Column 11,
Line 25, after "RSV" delete "10";
Line 45, change "nassally" to -- nasally --;

Column 13,
Line 5, change "E:.:tens-ve" to -- Extensive --;

Column 14,
Line 9, change "neutralisat ion" to -- neutralization --;
Line 17, at the end of the line of "SEQ ID NO: 9" add -- R A --;
Line 19, at the end of the line of "SEQ ID NO: 10" add -- S I --;
Line 21, at the end of the line of "SEQ ID NO: 11" add -- N K --;
Line 23, at the end of the line of "SEQ ID NO: 12" add -- K K --;
Line 39, in "TABLE 2" change "$^a$Peptides" to -- $^a$ = Peptides --;
Line 45, in "TABLE 3" change "($\overline{\geq}$4x)" to -- ($\geq$4x) --;
Lines 59-61, move the column heading for column 1 on lines 62-64 to lines 59-61
-- human serum (epidemic '94 Madrid) --;

UNITED STATES PATENT AND TRADEMARK OFFICE
CERTIFICATE OF CORRECTION

PATENT NO.    : 6,077,511
DATED         : June 20, 2000
INVENTOR(S)   : Langedijk It is certified that error appears in the above-identified patent and that said Letters Patent is hereby corrected as shown below:

<u>Column 15,</u>
Lines 5-7, insert the column heading for column 1, -- human serum (epidemic '94 Madrid) --;
Line 14, change ">169" to -- >160 --; and
Line 28, change "1250" to -- 1280 --.

Signed and Sealed this

Twenty-first Day of January, 2003

JAMES E. ROGAN
*Director of the United States Patent and Trademark Office*

```
                        SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 1:

His Gln Asp His Asn Asn Phe Gln Thr Leu Pro Tyr Val Pro Cys Ser
1               5                   10                  15

Thr Cys Glu Gly Asn Leu Ala Cys Leu Ser Leu Cys
            20                  25

(2) INFORMATION FOR SEQ ID NO: 2:

(i) SEQUENCE CHARACTERISTICS:
        (A) LENGTH: 28 amino acids
        (B) TYPE: amino acid
```

(C) STRANDEDNESS: single
                (D) TOPOLOGY: linear (ii) MOLECULE TYPE: peptide (iii) HYPOTHETICAL: NO (xi) SEQUENCE DESCRIPTION: SEQ ID NO: 2:

Gln Gln Asp Tyr Ser Asp Phe Gln Ile Leu Pro Tyr Val Pro Cys Asn
1               5                  10                  15

Ile Cys Glu Gly Asp Ser Ala Cys Leu Ser Leu Cys
            20                  25

(2) INFORMATION FOR SEQ ID NO: 3:

(i) SEQUENCE CHARACTERISTICS:
                (A) LENGTH: 28 amino acids
                (B) TYPE: amino acid
                (C) STRANDEDNESS: single
                (D) TOPOLOGY: linear (ii) MOLECULE TYPE: peptide (iii) HYPOTHETICAL: NO (xi) SEQUENCE DESCRIPTION: SEQ ID NO: 3:

Pro Lys Asp Asp Tyr His Phe Glu Val Phe Asn Phe Val Pro Cys Ser
1               5                  10                  15

Ile Cys Gly Asn Asn Gln Leu Cys Lys Ser Ile Cys
            20                  25

(2) INFORMATION FOR SEQ ID NO: 4:

(i) SEQUENCE CHARACTERISTICS:
                (A) LENGTH: 28 amino acids
                (B) TYPE: amino acid
                (C) STRANDEDNESS: single
                (D) TOPOLOGY: linear (ii) MOLECULE TYPE: peptide (iii) HYPOTHETICAL: NO (xi) SEQUENCE DESCRIPTION: SEQ ID NO: 4:

Pro Asn Asn Asp Phe His Phe Glu Val Phe Asn Phe Val Pro Cys Ser
1               5                  10                  15

Ile Cys Ser Asn Asn Pro Thr Cys Trp Ala Ile Cys
            20                  25

(2) INFORMATION FOR SEQ ID NO: 5:

(i) SEQUENCE CHARACTERISTICS:
                (A) LENGTH: 32 amino acids
                (B) TYPE: amino acid
                (C) STRANDEDNESS: single
                (D) TOPOLOGY: linear (ii) MOLECULE TYPE: peptide (iii) HYPOTHETICAL: NO (xi) SEQUENCE DESCRIPTION: SEQ ID NO: 5:

Asn His Gln Asp His Asn Asn Phe Gln Thr Leu Pro Tyr Val Pro Cys
1               5                  10                  15

Ser Thr Cys Glu Gly Asn Leu Ala Cys Leu Ser Leu Cys His Ile Glu
            20                  25                  30

(2) INFORMATION FOR SEQ ID NO: 6:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 6:

```
Ile Gln Gln Asp Tyr Ser Asp Phe Gln Ile Leu Pro Tyr Val Pro Cys
 1               5                  10                  15

Asn Ile Cys Glu Gly Asp Ser Ala Cys Leu Ser Leu Cys Gln Asp Arg
             20                  25                  30
```

(2) INFORMATION FOR SEQ ID NO: 7:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 7:

```
Lys Pro Lys Asp Asp Tyr His Phe Glu Val Phe Asn Phe Val Pro Cys
 1               5                  10                  15

Ser Ile Cys Gly Asn Asn Gln Leu Cys Lys Ser Ile Cys Lys Thr Ile
             20                  25                  30
```

(2) INFORMATION FOR SEQ ID NO: 8:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 8:

```
Lys Pro Asn Asn Asp Phe His Phe Glu Val Phe Asn Phe Val Pro Cys
 1               5                  10                  15

Ser Ile Cys Ser Asn Asn Pro Thr Cys Trp Ala Ile Cys Lys Arg Ile
             20                  25                  30
```

(2) INFORMATION FOR SEQ ID NO: 9:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 9:

```
Glu Asn His Gln Asp His Asn Asn Phe Gln Thr Leu Pro Tyr Val Pro
 1               5                  10                  15
```

```
Cys Ser Thr Cys Glu Gly Asn Leu Ala Cys Leu Ser Leu Cys His Ile
            20                  25                  30

Glu Thr Glu Arg Ala
        35

(2) INFORMATION FOR SEQ ID NO: 10:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 10:

Glu Ile Gln Gln Asp Tyr Ser Asp Phe Gln Ile Leu Pro Tyr Val Pro
1               5                   10                  15

Cys Asn Ile Cys Glu Gly Asp Ser Ala Cys Leu Ser Leu Cys Gln Asp
            20                  25                  30

Arg Ser Glu Ser Ile
        35

(2) INFORMATION FOR SEQ ID NO: 11:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 11:

Lys Lys Pro Lys Asp Asp Tyr His Phe Glu Val Phe Asn Phe Val Pro
1               5                   10                  15

Cys Ser Ile Cys Gly Asn Asn Gln Leu Cys Lys Ser Ile Cys Lys Thr
            20                  25                  30

Ile Pro Ser Asn Lys
        35

(2) INFORMATION FOR SEQ ID NO: 12:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 12:

Asn Lys Pro Asn Asn Asp Phe His Phe Glu Val Phe Asn Phe Val Pro
1               5                   10                  15

Cys Ser Ile Cys Ser Asn Asn Pro Thr Cys Trp Ala Ile Cys Lys Arg
            20                  25                  30

Ile Pro Asn Lys Lys
        35
```

```
(2) INFORMATION FOR SEQ ID NO: 13:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 13:

Ser Ile Cys Ser Asn Asn Pro Thr Cys Trp Ala Ile Cys Lys Arg Ile
1               5                   10                  15
```